US012213842B2

(12) United States Patent
Lessard et al.

(10) Patent No.: US 12,213,842 B2
(45) Date of Patent: Feb. 4, 2025

(54) APPARATUS FOR PREVENTING DEVICE DEPLOYMENT FAILURE

(71) Applicant: Teleflex Life Sciences LLC, Wilmington, DE (US)

(72) Inventors: Kevin Alexander Lessard, San Francisco, CA (US); Christopher Zaler, Los Gatos, CA (US); Jolene Cutts, San Francisco, CA (US); Alexander Charles Gordon, San Carlos, CA (US); Maheshwara Rao, Oakland, CA (US); Mitchell C. Barham, San Mateo, CA (US)

(73) Assignee: Teleflex Life Sciences LLC, Wilmington, DE (US)

( * ) Notice: Subject to any disclaimer, the term of this patent is extended or adjusted under 35 U.S.C. 154(b) by 28 days.

(21) Appl. No.: 18/188,761

(22) Filed: Mar. 23, 2023

(65) Prior Publication Data

US 2023/0218362 A1    Jul. 13, 2023

Related U.S. Application Data

(63) Continuation of application No. 17/178,679, filed on Feb. 18, 2021, now Pat. No. 11,701,197.

(60) Provisional application No. 62/979,903, filed on Feb. 21, 2020.

(51) Int. Cl.
*A61B 17/04* (2006.01)
*A61B 17/00* (2006.01)
*A61B 17/06* (2006.01)
*A61B 90/00* (2016.01)

(52) U.S. Cl.
CPC ........ *A61B 90/03* (2016.02); *A61B 17/00234* (2013.01); *A61B 17/0401* (2013.01); *A61B 17/0469* (2013.01); *A61B 17/06* (2013.01); *A61B 90/08* (2016.02); *A61B 2017/00274* (2013.01); *A61B 2090/034* (2016.02); *A61B 2090/0811* (2016.02)

(58) Field of Classification Search
CPC ............ A61B 17/0469; A61B 17/0482; A61B 17/0483; A61B 17/06; A61B 90/03; A61B 2090/032
See application file for complete search history.

(56) References Cited

U.S. PATENT DOCUMENTS

| 4,896,678 A | 1/1990 | Ogawa |
| 5,499,994 A | 3/1996 | Tihon et al. |
| 5,897,564 A | 4/1999 | Schulze et al. |

(Continued)

FOREIGN PATENT DOCUMENTS

| CN | 105852938 A | 8/2016 |
| CN | 109675177 A | 4/2019 |

(Continued)

OTHER PUBLICATIONS

Office Action mailed Feb. 22, 2023, in Japanese Patent Appln. 2022-522645.

(Continued)

*Primary Examiner* — Todd J Scherbel
(74) *Attorney, Agent, or Firm* — Dorsey & Whitney LLP

(57) ABSTRACT

An apparatus for preventing deployment failure or damage of a movable portion of a treatment device via a force limiting element in the treatment device.

18 Claims, 7 Drawing Sheets

(56) References Cited

U.S. PATENT DOCUMENTS

| | | | |
|---|---|---|---|
| 6,068,624 A | 5/2000 | Benecke et al. |
| 7,645,286 B2 | 1/2010 | Catanese et al. |
| 7,758,594 B2 | 7/2010 | Lamson et al. |
| 7,766,923 B2 | 8/2010 | Catanese et al. |
| 7,905,889 B2 | 3/2011 | Catanese et al. |
| 7,938,046 B2 | 5/2011 | Nino et al. |
| 7,951,158 B2 | 5/2011 | Catanese et al. |
| 8,007,503 B2 | 8/2011 | Catanese et al. |
| 8,157,815 B2 | 4/2012 | Catanese et al. |
| 8,216,254 B2 | 7/2012 | McLean et al. |
| 8,333,776 B2 | 12/2012 | Cheng et al. |
| 8,343,187 B2 | 1/2013 | Lamson et al. |
| 8,394,110 B2 | 3/2013 | Catanese et al. |
| 8,425,535 B2 | 4/2013 | McLean et al. |
| 8,663,243 B2 | 3/2014 | Lamson et al. |
| 8,715,239 B2 | 5/2014 | Lamson et al. |
| 8,715,298 B2 | 5/2014 | Catanese et al. |
| 8,900,252 B2 | 12/2014 | Lamson et al. |
| 8,936,609 B2 | 1/2015 | Catanese et al. |
| 8,939,996 B2 | 1/2015 | Cheng et al. |
| 9,320,511 B2 | 4/2016 | McLean et al. |
| 9,549,739 B2 | 1/2017 | Catanese et al. |
| 9,931,192 B2 | 4/2018 | McLean et al. |
| 10,105,132 B2 | 10/2018 | Amson et al. |
| 10,299,780 B2 | 5/2019 | Catanese et al. |
| 10,702,261 B2 | 7/2020 | Stiggelbout |
| 11,701,197 B2 * | 7/2023 | Lessard .................. A61B 90/03 606/139 |
| 2003/0229263 A1 | 12/2003 | Connors et al. |
| 2004/0181235 A1 | 9/2004 | Daignault et al. |
| 2005/0256530 A1 | 11/2005 | Petros |
| 2006/0195008 A1 | 8/2006 | Whalen et al. |
| 2007/0260257 A1 | 11/2007 | Phan |
| 2008/0262424 A1 | 10/2008 | Hooft |
| 2009/0112234 A1 | 4/2009 | Crainich et al. |
| 2010/0063351 A1 | 3/2010 | Witzmann et al. |
| 2010/0191045 A1 | 7/2010 | Gobron et al. |
| 2010/0256442 A1 | 10/2010 | Ogdahl et al. |
| 2010/0261950 A1 | 10/2010 | Und et al. |
| 2010/0286717 A1 | 11/2010 | Heinrich et al. |
| 2010/0298831 A1 | 11/2010 | Browne et al. |
| 2011/0024145 A1 | 2/2011 | Click et al. |
| 2011/0082471 A1 | 4/2011 | Holcomb et al. |
| 2011/0105841 A1 | 5/2011 | Kutikov et al. |
| 2011/0172755 A1 | 7/2011 | Nelson et al. |
| 2011/0276081 A1 | 11/2011 | Kilemnik |
| 2012/0041533 A1 | 2/2012 | Bertolino et al. |
| 2012/0041534 A1 | 2/2012 | Clerc et al. |
| 2012/0245600 A1 | 9/2012 | McLean et al. |
| 2012/0265006 A1 | 10/2012 | Makower et al. |
| 2013/0046338 A1 | 2/2013 | Suzuki et al. |
| 2013/0268001 A1 | 10/2013 | Catanese et al. |
| 2013/0296889 A1 | 11/2013 | Tong et al. |
| 2014/0005473 A1 | 1/2014 | Catanese et al. |
| 2014/0031835 A1 | 1/2014 | Viker et al. |
| 2014/0180067 A1 | 6/2014 | Stigall et al. |
| 2014/0275756 A1 | 9/2014 | Bender et al. |
| 2014/0296881 A1 | 10/2014 | Ranucci et al. |
| 2015/0025652 A1 | 1/2015 | McLean et al. |
| 2015/0127050 A1 | 5/2015 | Lamson et al. |
| 2015/0351743 A1 | 12/2015 | Stiggelbout |
| 2016/0022265 A1 | 1/2016 | Kawaura et al. |
| 2016/0045297 A1 | 2/2016 | Siegel et al. |
| 2016/0095685 A1 | 4/2016 | Vemuri et al. |
| 2017/0000598 A1 | 1/2017 | Bachar |
| 2017/0112489 A1 | 4/2017 | Shelton, IV et al. |
| 2017/0135830 A1 | 5/2017 | Harkin et al. |
| 2017/0156723 A1 | 6/2017 | Keating et al. |
| 2017/0367748 A1 | 12/2017 | Plotkin |
| 2018/0049816 A1 | 2/2018 | Shelton, IV et al. |
| 2018/0103945 A1 | 4/2018 | Ciulla et al. |
| 2018/0318114 A1 | 11/2018 | Huang et al. |
| 2019/0125334 A1 | 5/2019 | Tong et al. |
| 2019/0365362 A1 | 12/2019 | Ralph |
| 2020/0038213 A1 | 2/2020 | Bly et al. |
| 2020/0121442 A1 | 4/2020 | Askeland |
| 2021/0145619 A1 | 5/2021 | Bly et al. |
| 2021/0161641 A1 | 6/2021 | Bachar |
| 2021/0161642 A1 | 6/2021 | Jen et al. |
| 2021/0259799 A1 | 8/2021 | Lessard et al. |
| 2021/0307641 A1 | 10/2021 | Rumbles et al. |
| 2022/0000445 A1 | 1/2022 | Datta et al. |
| 2022/0024145 A1 | 1/2022 | Itsuno et al. |
| 2022/0031357 A1 | 2/2022 | Cutts et al. |
| 2022/0031358 A1 | 2/2022 | Yarra et al. |
| 2022/0031389 A1 | 2/2022 | Fischell et al. |
| 2022/0061834 A1 | 3/2022 | Chung et al. |
| 2022/0125499 A1 | 4/2022 | Hoey et al. |
| 2022/0133462 A1 | 5/2022 | Kilemnik |
| 2022/0142464 A1 | 5/2022 | Petroff et al. |
| 2022/0240925 A1 | 8/2022 | Epstein et al. |
| 2022/0249219 A1 | 8/2022 | Chung et al. |
| 2022/0265262 A1 | 8/2022 | Melsheimer |
| 2022/0273918 A1 | 9/2022 | Ghriallais et al. |
| 2022/0378577 A1 | 12/2022 | Anderson et al. |
| 2022/0395363 A1 | 12/2022 | Ghriallais et al. |
| 2023/0022482 A1 | 1/2023 | Dhavale |

FOREIGN PATENT DOCUMENTS

| | | |
|---|---|---|
| CN | 211156119 U | 8/2020 |
| CN | 112891032 A | 6/2021 |
| CN | 216221843 U | 4/2022 |
| DE | 102019101987 A1 | 7/2020 |
| JP | 63147449 | 6/1988 |
| JP | 2008093437 A | 4/2008 |
| JP | 2013517899 A | 5/2013 |
| JP | 2023502729 A | 1/2023 |
| KR | 101534820 B1 | 7/2015 |
| WO | 2011094299 A3 | 12/2011 |
| WO | 2012028843 A1 | 3/2012 |
| WO | 2012118011 A1 | 9/2012 |
| WO | 2017026167 A1 | 2/2017 |
| WO | 2021190092 A1 | 9/2021 |

OTHER PUBLICATIONS

PCT International Search Report mailed Jun. 9, 2021 in PCT application No. PCT/US2021/018487.

PCT Written Opinion mailed Jun. 9, 2021 in PCT application No. PCT/US2021/018487.

* cited by examiner

APPARATUS FOR PREVENTING DEVICE DEPLOYMENT FAILURE

CROSS REFERENCE TO RELATED APPLICATIONS

This application is a continuation of U.S. Non-Provisional patent application Ser. No. 17/178,679, filed Feb. 18, 2021, now U.S. Pat. No. 11,701,197, which claims the benefit of priority under 35 U.S.C. § 119(e) to U.S. Provisional Patent Application No. 62/979,903, filed on Feb. 21, 2020, entitled "Apparatus For Preventing Device Deployment Failure," each of which is incorporated herein by reference.

BACKGROUND OF THE INVENTION

The present invention relates generally to medical devices, and more particularly to apparatuses for preventing deployment failure of a movable portion of a treatment device, where the movable portion is involved in manipulating tissue or anatomical structures within the body of a human or animal subject for the purpose of treating diseases or disorders.

Various diseases or disorders of soft tissue and anatomical organs such as the uterus, intestine, and prostate can require surgical intervention with a treatment device to manipulate or remove abnormal, diseased, enlarged, or overgrown tissue. When such procedures are performed, the physician or surgeon may encounter non-target tissue, such as bone, calcifications, or other hard or solid anatomical structures, during introduction or manipulation of the treatment device at the interventional site of a patient, particularly when the interventional site is in close proximity to a soft-hard tissue interface.

One such interventional site that includes a soft-hard tissue interface is the anatomical region defined by the prostatic urethra, prostate, and pelvic bone commonly accessed during prostate resection procedures for the treatment of urological diseases or disorders such as Benign Prostatic Hyperplasia (BPH). BPH is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

The prostate gland enlarges throughout a man's life. In some men, the prostatic capsule around the prostate gland may prevent the prostate gland from enlarging further. This causes the inner region of the prostate gland to squeeze the urethra. This pressure on the urethra increases resistance to urine flow through the region of the urethra enclosed by the prostate. Thus, the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, and an urgent need to urinate.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine etc.) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery, and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Surgical procedures for treating BPH symptoms include Transurethal Resection of Prostate (TURP), Transurethral Electrovaporization of Prostate (TVP), Transurethral Incision of the Prostate (TUIP), Laser Prostatectomy and Open Prostatectomy.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

Many current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry a lower risk of adverse effects are also associated with a lower reduction in the symptom score. While several of these procedures can be conducted with local analgesia in an office setting, the patient does not experience immediate relief and in fact often experiences worse symptoms for weeks after the procedure until the body begins to heal. Additionally, all device approaches require a urethral catheter placed in the bladder, in some cases for weeks. In some cases, catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

New devices and methods have been developed for various procedures to lift, compress, support, reposition, ablate, or otherwise alter prostatic tissue in a discrete procedure or in combination with treating BPH. Such devices and methods are disclosed in U.S. Pat. Nos. 7,645,286; 7,758,594; 7,766,923; 7,905,889; 7,951,158; 8,007,503; 8,157,815; 8,216,254; 8,333,776; 8,343,187; 8,394,110; 8,425,535; 8,663,243; 8,715,239; 8,715,298; 8,900,252; 8,936,609; 8,939,996; 9,320,511; 9,549,739; 10,105,132; and 10,299,780 which are hereby incorporated by reference herein in their entireties. During some procedures, a movable portion of the treatment device can strike bone, calcifications, or other solid or hard anatomical structures, causing damage, such as breakage, bowing, or buckling, to the movable portion or other parts of the device operatively connected to the movable portion. Such damage may prevent proper treatment.

In addition to devices and methods to treat BPH, there are devices and methods to treat other conditions in which a treatment device uses a movable portion to manipulating tissue or anatomical structures within the body of a human or animal subject for the purpose of treating diseases or disorders. Such methods and devices may also experience scenarios in which the movable portion suffers damage, or the intended treatment is frustrated, by the movable portion, or other parts of the device operatively connected to the movable portion, contacting solid or hard anatomical structures.

There remains a need for development of new systems for preventing damage to movable portions of treatment devices when such portions, or other parts of the device operatively connected to the movable portion, encounter non-target tissue or structures. The present disclosure addresses these needs.

SUMMARY OF THE INVENTION

Embodiments of the present invention are directed towards an apparatus for preventing damage to a treatment device for manipulating tissues and anatomical or other structures within the body of a human or animal subject for the purpose of treating diseases or disorders.

Embodiments of the present invention include an apparatus for mitigating damage to a treatment device, where the apparatus includes a treatment tool coupled to a movable assembly at a proximal portion of the treatment tool and a force limiting element connected to the proximal portion of the treatment tool and connected to the movable assembly. The force limiting element allows movement of the proximal portion of the treatment tool in a proximal direction with respect to the movable assembly while maintaining the coupling between the movable assembly and the proximal portion of the treatment tool when forces experienced by the treatment tool increase to a predetermined amount of force.

In some embodiments, the force limiting element comprises a spring, a reversibly engageable connector, or both. In some embodiments, the predetermined amount of force is the amount of force needed to extend the spring. In some embodiments, the predetermined amount of force is the amount of force disengage the reversibly engageable connector.

In some embodiments, the proximal portion of the treatment tool further comprises a friction element that conditionally prevents movement of the proximal portion of the treatment tool with respect to the movable assembly. In some embodiments, the force limiting element assists in moving the proximal portion of the treatment tool in a distal direction with respect to the movable assembly when forces experienced by the treatment tool decrease below the predetermined amount of force.

In some embodiments, the treatment tool is a suture or a needle.

In some embodiments, the apparatus further comprises an indicator, wherein the indicator indicates when the treatment tool has been completely deployed. In some embodiments, the indicator comprises a visual, audible, or tactile indicator.

Other features and advantages of embodiments of the present invention will become apparent from the following description, taken in conjunction with the accompanying drawings, which illustrate, by way of example, certain principles of the invention.

DETAILED DESCRIPTION OF ILLUSTRATIVE EMBODIMENTS

Figure 1:
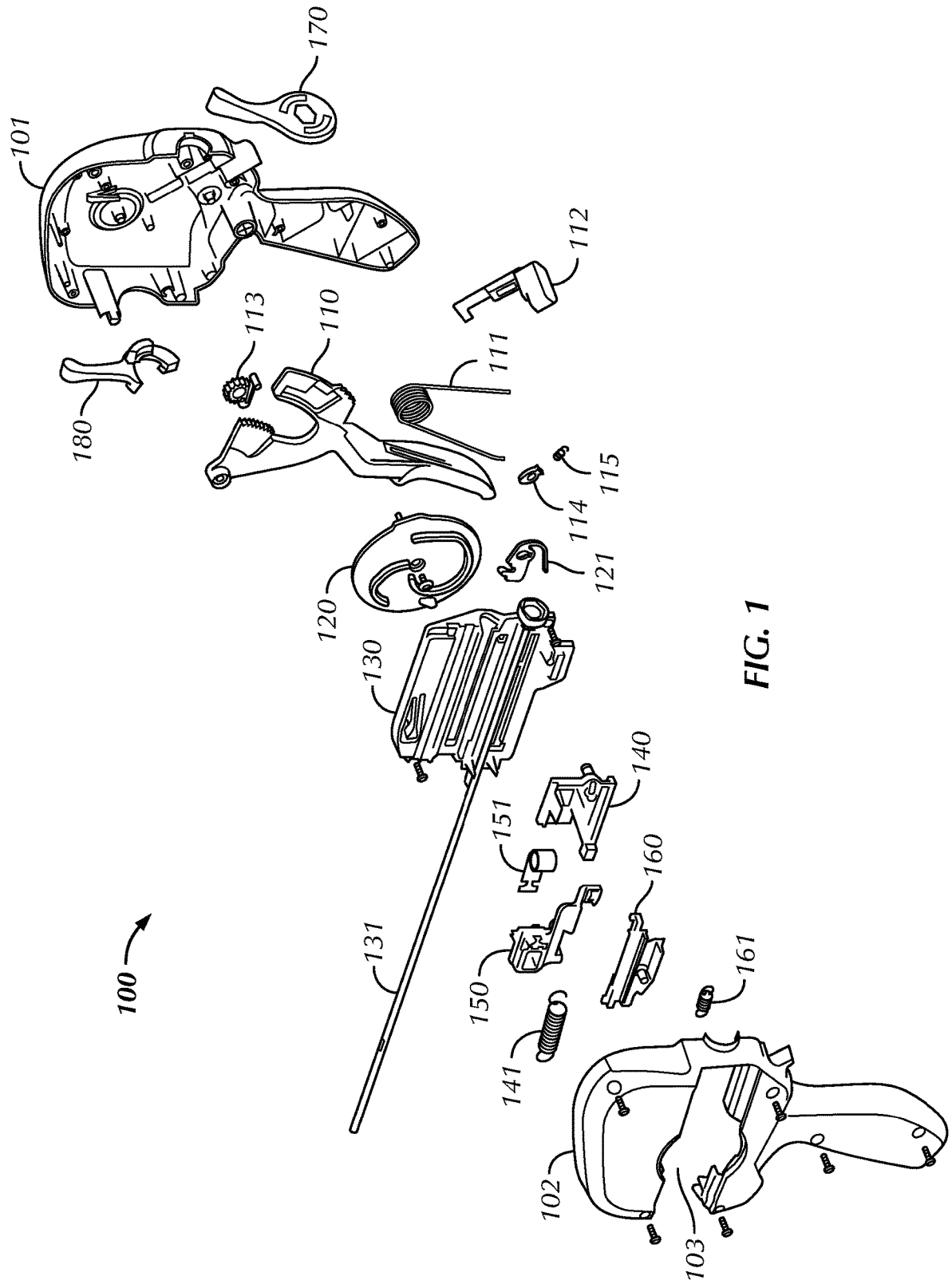
FIG. 1 is an exploded, isometric view of a handle of a system for treating benign prostatic hyperplasia.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

The use of "adapted to" or "configured to" herein is meant as open and inclusive language that does not foreclose devices adapted to or configured to perform additional tasks or steps. The use of "proximal" and "distal" herein refers to relative positions with respect to a user of the elongate, minimally invasive devices, where "proximal" means relatively towards the user and "distal" means relatively away from the user. Headings, lists, and numbering included herein are for ease of explanation only and are not meant to be limiting.

Generally, embodiments of the apparatus of the present disclosure prevent damage to a treatment device. Treatment devices delivered to the interventional site of a patient can be equipped with various tools which manipulate, ablate, or otherwise alter tissue. Such tools can include, but are not limited to, needles, cutting blades, vacuums, grasping arm assemblies, expandable cutting members, blunt dissectors, noose or ligature clips, articulating heads with an integral or retractable blade, helical blades, electrodes for delivery of radiofrequency energy, cutting wires or rings, electrocauterizing probes, or staple or suture delivery heads. These tools can be advanced from a working channel, needle, or puncturing element at the distal end of an elongate member of the treatment device such that the tool is unsheathed from the elongate member. In some embodiments, the tool can be attached to the distal end of the elongate member and does not require unsheathing.

Turning now to the figures, which are provided by way of example and not limitation, embodiments of the present disclosure is directed to an apparatus for limiting and/or dampening forces applied to a movable portion of a treatment device. Certain embodiments of the present disclosure additionally or alternatively are directed to an apparatus for accommodating relative changes in length between two movable portions of a treatment device as those movable portions move with respect to each other. In many cases, embodiments of the present disclosure can prevent damage to movable portions of a treatment device while the treatment device is being used for manipulating tissues and anatomical or other structures within the body of a human or animal subject for the purpose of treating diseases or disorders. The disclosed apparatus can be implemented in various treatment devices employed for various medical purposes including, but not limited to, retracting, lifting, compressing, approximating, supporting, remodeling, repositioning, ablating, or otherwise altering tissues, organs, anatomical structures, grafts, or other material found within the body of a human or animal subject. In certain embodiments, treatment devices are intended to displace, compress, retract, or destroy tissue of the prostate to facilitate treatment of diseases or disorders such as Benign Prostatic Hyperplasia (BPH).

Referring now to FIG. 1, a BPH treatment device handle 100 is shown in an exploded, isometric view. The BPH treatment device handle 100 includes a right handle case 101, a left handle case 102, and a cartridge bay 103 formed in left handle case 102. The treatment device handle 100 is designed to transmit the energy stored in several springs within the treatment device handle 100 to a cartridge (shown in FIG. 2A) to enable the treatment of BPH in a patient.

The treatment device handle 100 includes a handle trigger assembly 110, which is operatively connected to a handle trigger spring 111 such that the handle trigger spring 111 provides force sufficient to return the handle trigger assembly to its initial position after the handle trigger assembly 110 has been squeezed and released by a user. A ratchet 114, which is connected to a ratchet spring 115, affects the motion of the handle trigger assembly 110 such that the handle trigger assembly 110 does not return to its initial position prior to being squeezed to a predetermined amount by a user. A safety 112 is connected to the handle trigger assembly 110 to ensure that the handle trigger assembly 110 is not operated accidentally. The handle trigger assembly 110 is connected to a drive gear 113, which is connected to a cam wheel 120.

The cam wheel 120 rotates about a central axis and, via structures and features on the cam wheel, triggers certain motions within the treatment device handle 100 as the cam wheel 120 rotates. There are multiple sleds operatively connected to the cam wheel 120, and the sled move in a linear direction along a lateral axis of the treatment device handle 100. There are multiple springs that impart force to the multiple sleds to general the motion and provide the mechanical energy sufficient to delivery an implant to treat BPH. A cartridge (depicted in FIG. 2A) includes multiple tab assemblies that mate with the sleds via slots in the sled such that the motion and energy imparted by the operation of the mechanisms in the handle (such as the springs) is transmitted to the mechanisms in the cartridge.

Specifically, an implant trigger 121 is operatively connected to the cam wheel 120 and an implant sled 160, which is connected to an implant spring 161 that provides energy related to the delivery of the implant. A needle sled 140 is operatively connected to the cam wheel 120, and a needle sled spring 141 provides energy related to the delivery of the implant. A suture sled 150 is operatively connected to the cam wheel 120, and a suture sled spring 151 provides energy related to the delivery of the implant. In each of these cases, a sled may move at sufficient velocity such that if a portion of the system connected to the sled encounters non-target hard tissue or other hard obstacles, damage to the device may result.

The treatment device handle 100 includes various other parts, such as a cover plate 130, an endoscope tube 131, a scope lock 170, a sheath lock 180, and various screws and/or fasteners to assemble the handle. The cover plate 130 provides the interior base for the cartridge bay 103. The endoscope tube 131, the scope lock 170, and the sheath lock 180 provide functionality for attaching an endoscope and other ancillary equipment (such as a surgical sheath) to facilitate the procedure.

Figure 2A:
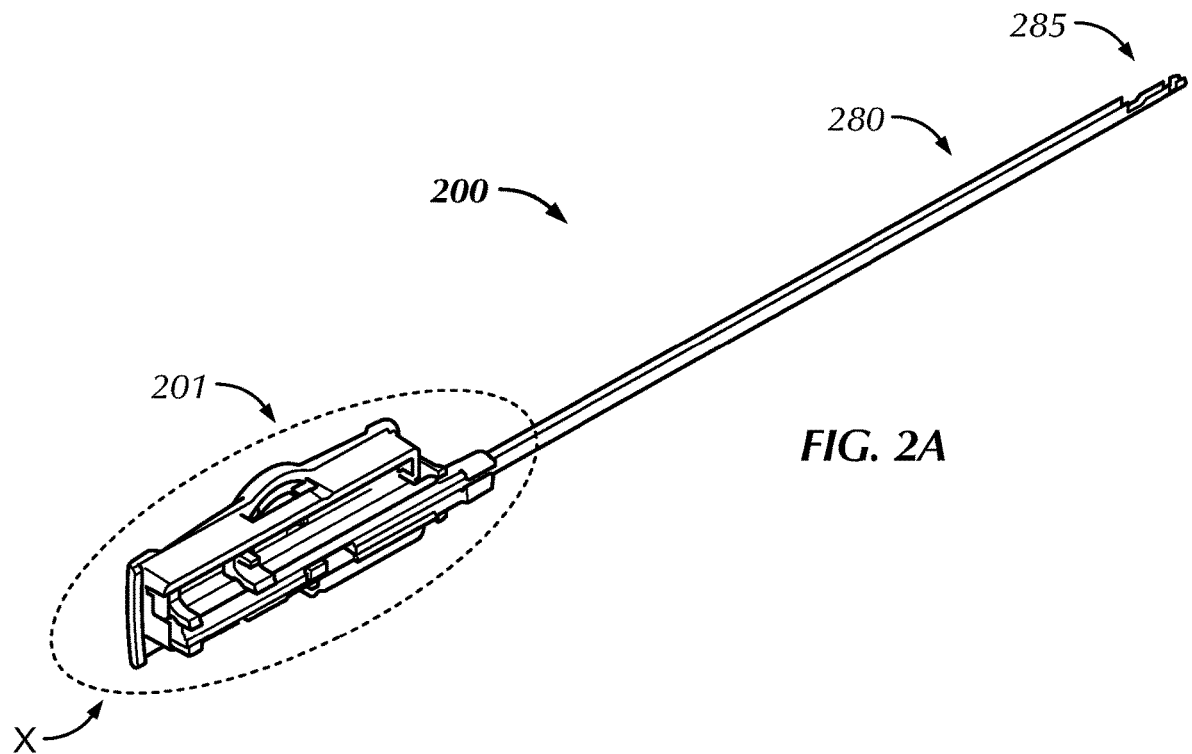
FIG. 2A is an isometric view of a cartridge of a system for treating benign prostatic hyperplasia.

Referring now to FIG. 2A, which shows an isometric view, a cartridge 200 is configured to couple with the treatment device handle 100. A cartridge housing 201 fits within the cartridge bay 103 of the treatment device handle 100 and a cartridge elongate assembly 280 runs parallel to the endoscope tube 131 of the treatment device handle 100. A distal portion 285 of the cartridge elongate assembly 280 includes exit ports for a needle, which is configured to facilitate placement of an implant. Thus, the treatment device handle 100 and the cartridge 200 together form a system for placing an implant for treating BPH. The springs and sleds in the treatment device handle 100 transmit energy and movement to tab assemblies in cartridge housing 201 to advance the needle into tissue and deploy the implant.

Figure 2B:
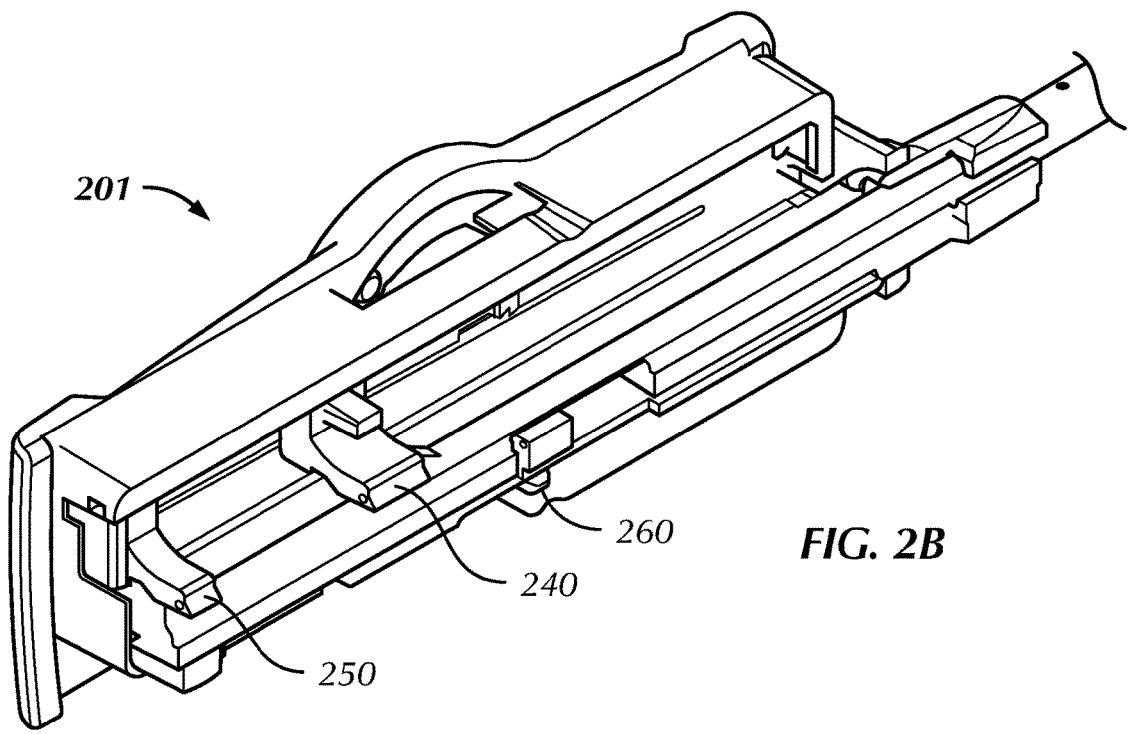
FIG. 2B is an isometric, enlarged view of a cartridge housing assembly of the cartridge of FIG. 2A.

Area X of FIG. 2A is shown in an enlarged, isometric view in FIG. 2B. The cartridge housing 201 includes a needle tab assembly 240, a suture tab assembly 250, and an implant tab assembly 260. These tab assemblies interact with the sleds and the springs in the treatment handle to deliver an implant for the treatment of BPH. Linear movement of these tab assemblies translates into mechanical movements at and, in some cases, beyond the distal portion 285 of the cartridge elongate assembly 280. For example, linear movement of the needle tab assembly 240 is related to movement of a penetrating needle from within the distal portion 285 of the cartridge elongate assembly 280 and into tissue, and further linear movement of the needle tab assembly 240 is related to retraction of the penetrating needle from tissue and back to within the distal portion 285 of the cartridge elongate assembly 280. Similarly, linear movement of the suture tab assembly 250 is related to movement of an implant from within the distal portion 285 of the cartridge elongate assembly 280 and into tissue, and further linear movement of the suture tab assembly 250 is related to deployment of the implant into tissue. And linear movement of the implant tab assembly 260 is related to assembly of the implant within tissue, including cutting a suture that is part of the implant.

The implant is deployed in tissue via the relative movement of the needle tab assembly 240 and the suture tab assembly 250. As a first step, the needle tab assembly 240 and the suture tab assembly 250 move together at the same rate in a distal direction. That is, the needle tab assembly 240 and the suture tab assembly 250 maintain their relative positions with respect to each other. Moving together, the needle tab assembly 240 and the suture tab assembly 250 advance a penetrating needle and an implant to a position within the tissue of a patient. The implant is connected with a suture, and this suture is coupled to a suture tube that is connected with the suture tab assembly 250. It is important during this first step that the needle tab assembly 240 and the suture tab assembly 250 maintain their relative positions with respect to each other so that the implant maintains its position within the needle and so that the implant can be deployed from the needle. The needle and the implant within the needle advance from the distal portion 285 of the cartridge elongate assembly 280.

As a second step, the needle tab assembly 240 moves proximally while the suture tab assembly 250 is held at its distal position. This relative movement of the needle tab assembly 240 with respect to the suture tab assembly 250 retracts the needle and deploys the implant. As a third step, the suture tab assembly 250 is retracted to position the implant and to place tension on the suture connected with the implant. As a third step, the implant tab assembly 260 moves distally to attach a proximal piece to the suture to complete the implant and to cut the suture, thereby fully deploying the implant.

The movement of the needle tab assembly 240, the suture tab assembly 250, and the implant tab assembly 260 is accomplished through the interaction of these tab assemblies with the springs and sleds in the treatment device handle. The springs and sleds cooperate with the cam wheel and other features of the treatment device handle to move the tab assemblies according to the steps disclosed herein.

The tab assemblies disclosed herein are connected with elements that extend along all or part of the cartridge elongate assembly 280. For example, the needle tab assembly is connected to a needle and the suture tab assembly is connected to a suture, and the needle and the suture are configured such that at least a portion of the needle and at least a portion of the suture can extend through the distal portion 285 of the cartridge elongate assembly 280 and into tissue. The needle tab assembly may or may not be directly connected to the needle and the suture tab assembly may or may not be directly connected to the suture. That is, there may be one or more intermediate structures that connect the part of the needle and/or the part of the suture that extend through the distal portion 285 of the cartridge elongate assembly 280 and into tissue. For example, the suture may be connected to the suture tab assembly via a suture tube, which can be made of material that is relatively more rigid than the suture to provide for the transmission of a pushing force along the relatively more flexible suture. As another example, the needle may be connected to the needle tab assembly via an over-molded section, which can be made of a less expensive material than the distal portion of the needle. Thus, the connections between the tab assemblies and the elements at the distal end of the cartridge elongate assembly can include tubes, over-molded sections, or equivalent intermediate portions.

In some embodiments, a fixed connection between the tab assemblies and the other features of the cartridge and implant may lead to certain undesirable outcomes. In certain situations, the relative movement of the features of the cartridge and implant may be impeded, which can result in an incomplete delivery of the implant. For example, the needle may encounter non-target tissue, such as bone, as the needle advances from the distal portion 285 of the cartridge elongate assembly 280. In this situation, the needle may bend or in some cases buckle as the needle encounters bone. When the needle bends or buckles, the relative positions between the end of the needle and the implant within the needle can change due to the higher friction created in the bent or buckled needle.

In normal implant delivery situations, the friction between the inner surface of the needle and the outer surface of the implant is balanced by the spring force transmitted from the suture sled spring through the suture sled to the suture tab assembly. This balance of frictional force and spring force keeps the implant and suture in the same position relative to the end of the needle. However, when the needle is bent or buckled, the friction force can increase such that the friction force exceeds the spring force. In this case, when the needle is retracted by the needle tab assembly, this greater friction force prevents the implant from being deployed out of the end of the needle. That is, the spring force is partially overcome by the friction force and the implant moves proximally with the retracting needle and does not completely emerge from the end of the needle. In other cases, the end of the needle may become blocked and the implant cannot emerge from the distal end of the needle.

One possible consequence of the friction force exceeding the spring force is damage at or near the proximal end of the suture. For example, although the suture and connected implant move proximally with the retracting needle as described above, the proximal end of the suture is being held fixed by the suture tab assembly. Because the proximal end of the suture is being held fixed while the distal end of the suture is moving proximally, the proximal end of the suture may buckle or be otherwise damaged. Such damage can prevent another attempt at deploying the implant. That is, if the suture was not damaged, then the needle could be retracted, the treatment device repositioned, and the needle deployed again in an attempt to avoid the non-target tissue that created the failed deployment. However, damage to the proximal end of the suture at or near the suture tab assembly may prevent proper functioning of the suture tab assembly during subsequent deployment attempts. Thus, it is helpful to alter the connection between the suture and the suture tab assembly to accommodate a situation where the frictional force at the distal end of the suture increases such that the suture and connected implant move proximally with the retracting needle. More generally, it is helpful to have a connection between the spring-loaded mechanical elements of a system and the elements beings driven by that spring-loaded force in the event that those driven elements encounter high friction or obstacles that prevent motion.

Figure 3A:
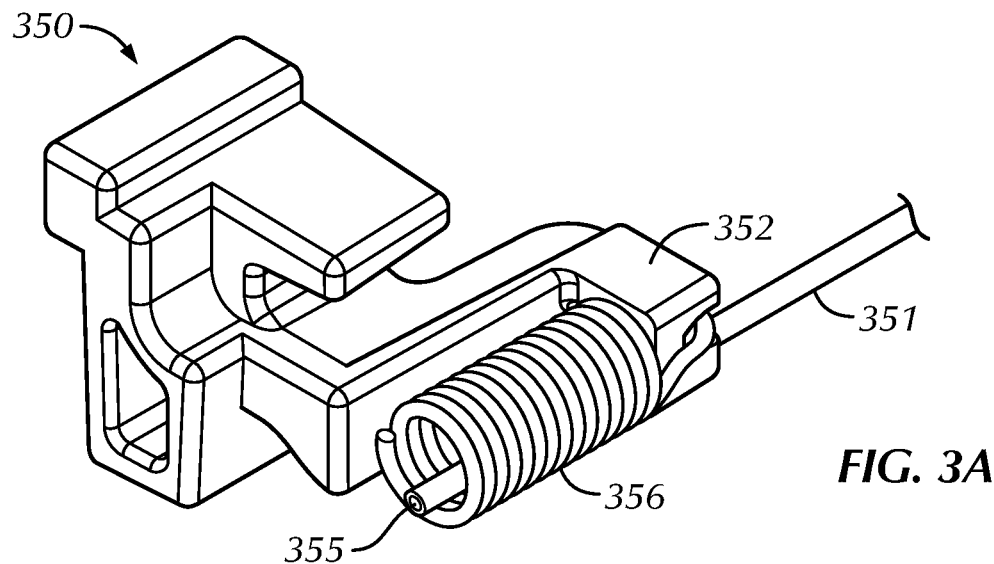
FIG. 3A is an isometric view of a force limiting assembly according to an embodiment of the invention.
Figure 3B:
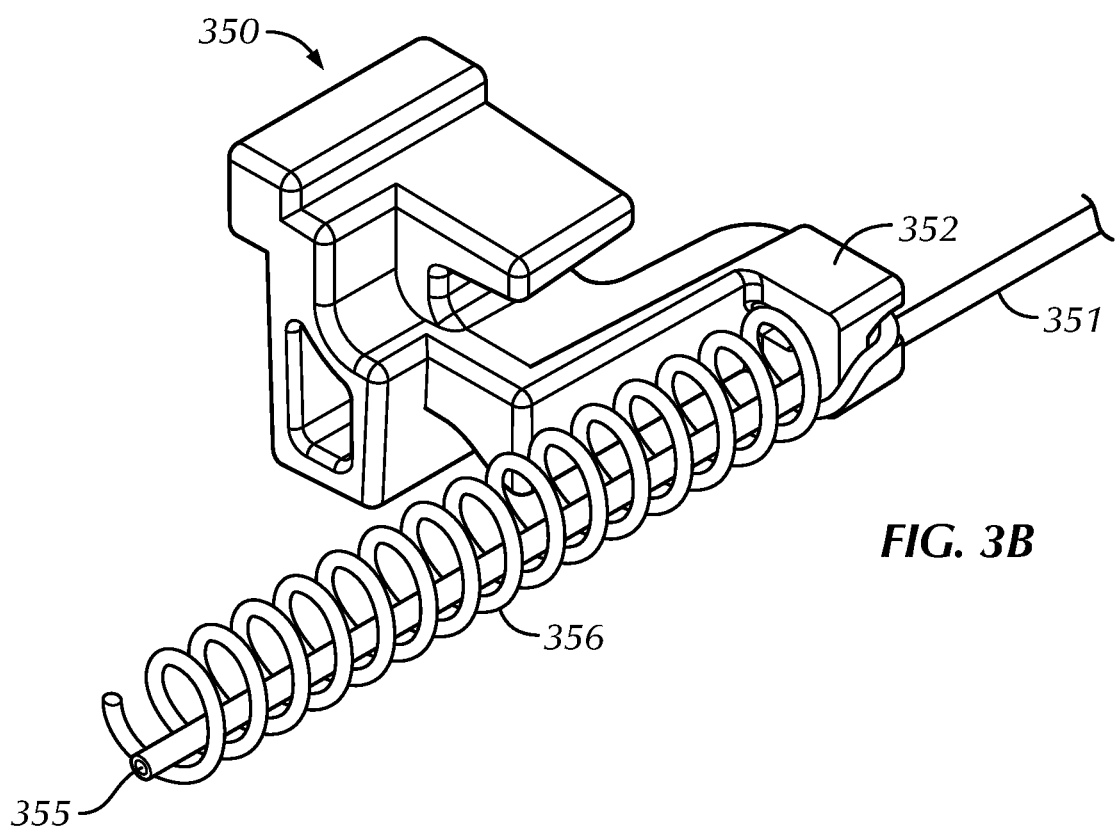
FIG. 3B is an isometric view of a force limiting assembly according to an embodiment of the invention.
Figure 4:
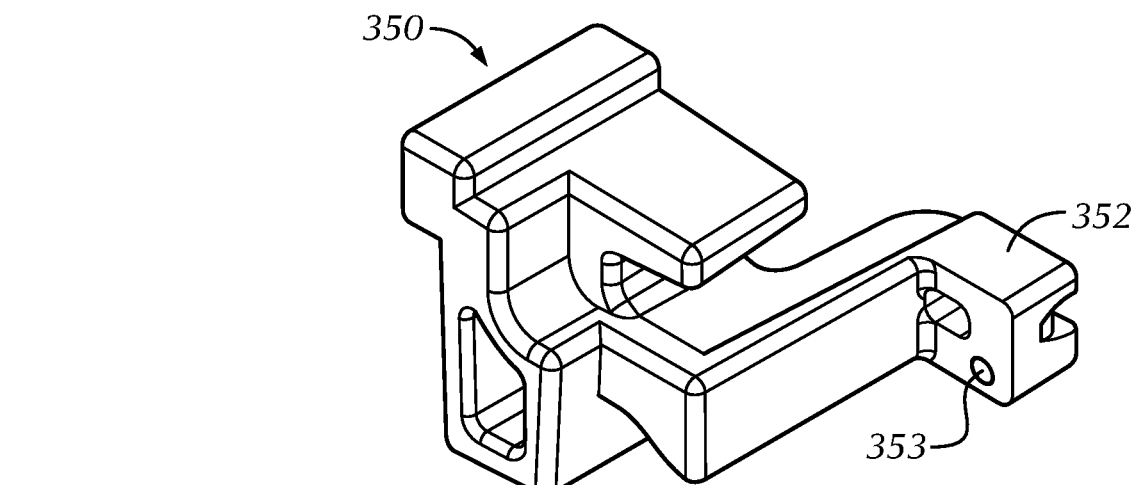
FIG. 4 is an isometric view of a portion of a force limiting assembly according to an embodiment of the invention.

FIG. 3A and FIG. 3B are isometric views of a force limiting assembly according to an embodiment of the invention. In this embodiment, the force limiting assembly is configured to modify the suture tab assembly presented herein. But the force limiting aspects of this force limiting assembly could be configured to modify the needle tab assembly, the implant tab assembly, or other assemblies where force limiting aspects are helpful for prevent damage to an element moved rapidly by a spring force or other force. In FIGS. 3A and 3B, a suture tab assembly 350 includes a suture tab assembly connection block 352, which is a connection area for a suture tube 351. A suture tube proximal end portion 355 couples with the suture tab assembly connection block 352 and with a force limiting spring 356. As illustrated in FIG. 4, the suture tab assembly connection block 352 can include a suture tab connection block passage 353. This suture tab connection block passage 353 is present in FIGS. 3A and 3B and the suture tube proximal end portion 355 passes through the suture tab connection block passage 353 as a way to couple the suture tube 351 to the suture tab assembly 350. While the suture tab connection block passage 353 is presented as a hole in the suture tab assembly connection block 352, other similar configurations are within the scope of this disclosure. The suture tab connection block passage 353 functions to couple the suture tube 351 to the suture tab assembly 350 while still allowing the force limiting spring 356 to engage in certain situations. Other coupling configurations that allow the force limiting spring 356 to engage in certain situations while also coupling the suture tube 351 to the suture tab assembly 350 may be used.

The force limiting spring 356 is joined to the suture tube proximal end portion 355 and to the suture tab assembly 350. In FIG. 3A and FIG. 3B, the force limiting spring 356 is illustrated as joined to the suture tab assembly 350 at the suture tab assembly connection block 352. However, the force limiting spring 356 may be joined to any portion of the suture tab assembly 350 provided that the force limiting spring 356 is configured to provide the force limiting functions disclosed herein. Similarly, the force limiting spring 356 may be joined to the suture tube 351 at any location provided that the force limiting spring 356 is configured to provide the force limiting functions disclosed herein. The force limiting spring 356 is illustrated in FIG. 3A and FIG. 3B as a coil type spring, but other types of springs may be employed provided that the spring is configured to function as a force limiting spring as disclosed herein.

FIG. 3A and FIG. 3B illustrates that force limiting spring 356 is a tension spring whose coils create a lumen through which the suture tube 351 extends. The ends of such a tension spring can include a hook or loop such as, but not limited to, machine hooks, cross over center hooks, side hooks, offset side hooks, V hooks, extended hooks, rectangular hooks, single or double twisted loop, open or closed loops, center loops, or side loops. In other embodiments, the force limiting spring 356 is a leaf spring or other spring mechanism. Indeed, the description of the force limiting spring 356 is meant to convey that the force limiting spring 356 is a mechanism capable of accommodating the proximal movement of the suture tube and then assisting in returning the suture tube to its initial position.

FIG. 3A illustrates the suture tab assembly 350 in a configuration where the force limiting spring 356 is in a relaxed position. In this position, the force limiting spring 356 is not engaged in limiting any forces on the suture tube 351. FIG. 3B illustrates the suture tab assembly 350 in a configuration where the force limiting spring 356 is in an extended position. The force limiting spring 356 is being extended by an increase in the frictional forces on the distal end of the suture. The increase in frictional forces could be due to the needle being bent or buckled, or by the distal end of the needle being blocked such that the implant and connected suture are not able to exit the needle as the needle tab assembly is being retracted. That is, there is a condition father distal on the suture that has transmitted forces proximally to the suture tab assembly 350. These transmitted forces are accommodating the force limiting spring 356 extending in a way that takes up the transmitted forces. In this way, the relative positions of the implant and connected suture and the distal end of the needle are preserved in a circumstance where those positions would have otherwise changed due to the increased friction and/or blockage at the distal portion of the needle.

Thus, the spring force can be considered a predetermined force that the friction force must overcome in order to engage the force limiting behavior of the force limiting spring. The force limiting spring may obeys Hooke's law such that the spring force scales linearly with the length of spring extension. The force limiting spring may also be a so-called "constant force" spring where for relatively small variations around an initial preloaded position the spring force is approximately constant.

Figure 5A:
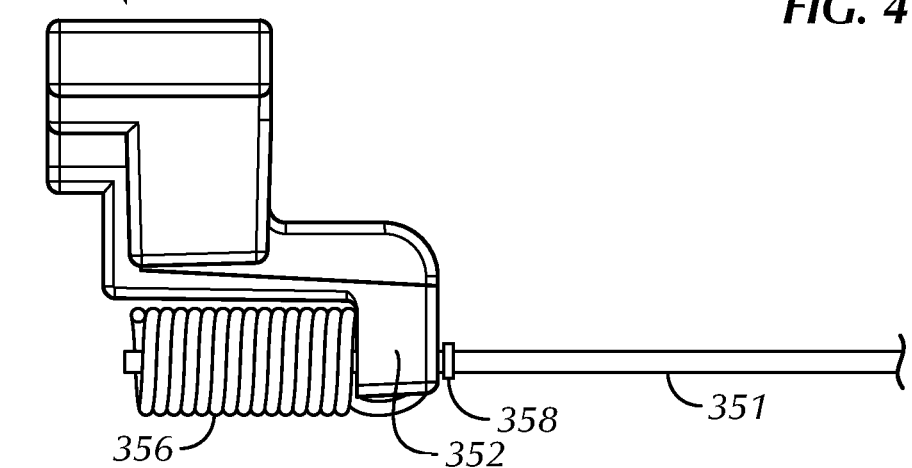
FIG. 5A is a top view of a force limiting assembly according to another embodiment of the invention.
Figure 5B:
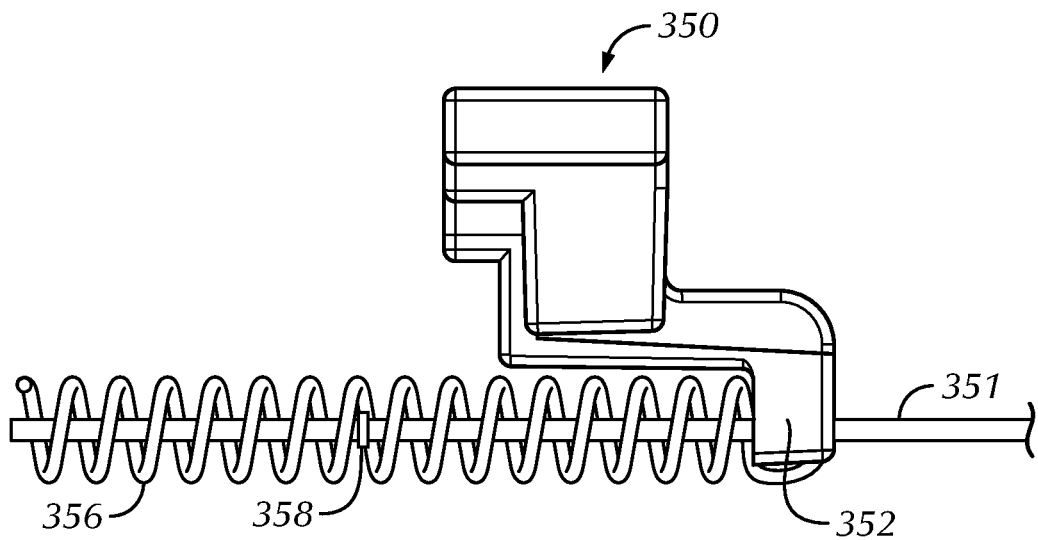
FIG. 5B is a top view of a force limiting assembly according to another embodiment of the invention.

FIG. 5A and FIG. 5B are top views of a force limiting assembly according to another embodiment of the invention. In this embodiment, the suture tube 351 includes a friction element 358 near the area at which the suture tube 351 is coupled with the suture tab assembly connection block 352. In some embodiments, the friction element 358 is a collar or similar structure that conditionally prevents the suture tube 351 from moving proximally through the suture tab assembly connection block 352 and engaging the force limiting spring 356. In some embodiments the friction element 352 is a flattened or crimped section of suture tube 351 such that the cross section of the suture tube 351 at the friction element 352 is larger in at least one radial direction that the rest of the suture tube 351.

The conditional nature of the friction element 358 is such that a minimum force is required to push the friction element 358 through the suture tab connection block passage 353. That is, the forces experienced by the suture or suture tube as a result of the needle being bent or buckled, or the distal end of the needle being blocked, must be greater than the force required to push the friction element 358 through the suture tab connection block passage 353. Thus, there are embodiments where the resting force of the force limiting spring 356 is sufficient to balance the forces experienced by the suture and/or suture tube and in those embodiments a friction element is not needed. But there are also embodiments where the use of a friction element is helpful or necessary to balance the forces experienced by the suture and/or suture tube and prevent unwanted engagement of the friction limiting spring.

In this regard, the suture tab connection block passage 353 functions as a slip fit for the friction element 358. The width of the friction element 358 is configured selected to allow for the friction element 358 to pass through the suture tab connection block passage 353 when sufficient force is applied to either the distal end of the suture tube (such as when the needle strikes bone or encounters other hard material) or the proximal end of the suture tube (such as when the force limiting spring 356 is returned to its initial position). The friction element 358 can also be calibrated based on the location and physical properties of non-target tissue that may be encountered during use of the treatment device at an interventional site of a patient.

Several of the embodiments disclosed herein rely on the force limiting spring to assist in returning the suture tube to its initial position. Proper deployment of an implant can then be attempted using the reset handle and cartridge system. There are also embodiments in which there is a mechanism for accommodating the increased frictional force and/or a blockage at the distal end of the needle and then the suture tube is manually returned to its initial position. In some embodiments, the system can be returned to an initial position via an actuator or trigger on the handle of the system.

Figure 6:
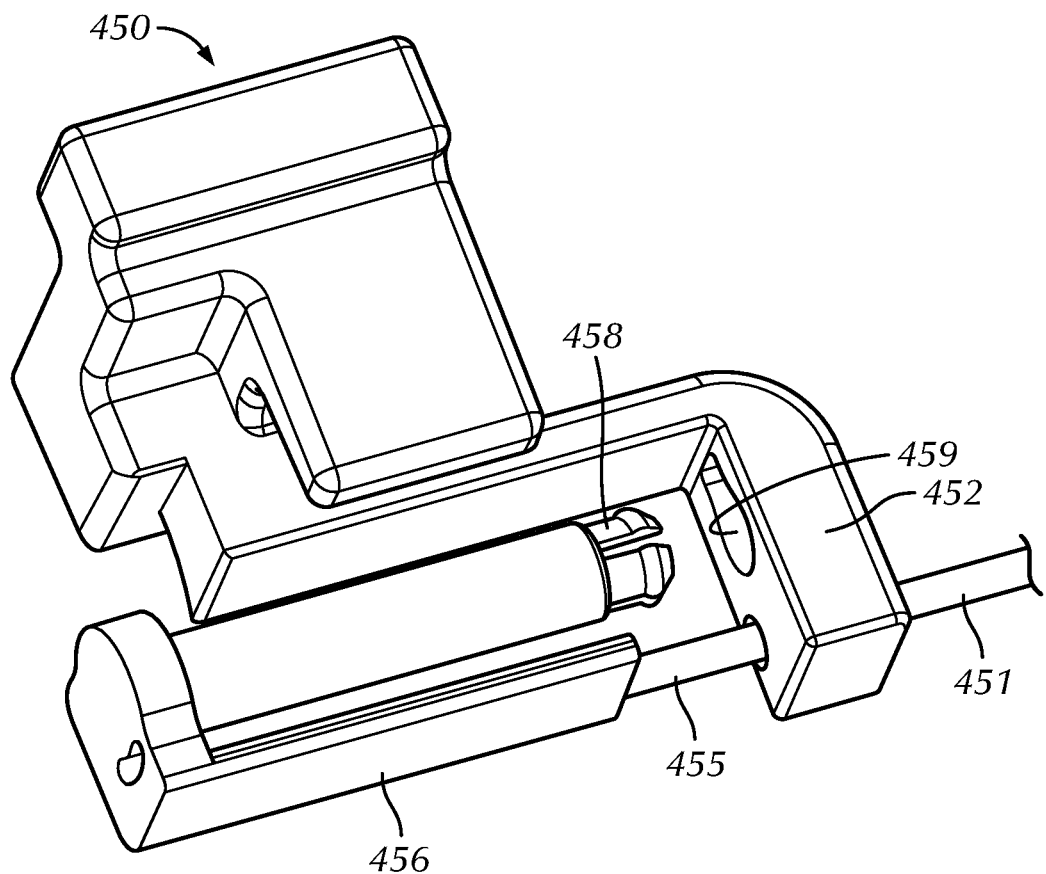
FIG. 6 is an isometric view of a force limiting connector according to another embodiment of the invention.

In FIG. 6, a suture tab assembly 450 includes a suture tab assembly connection block 452, which is a connection area for a suture tube 451. A suture tube proximal end portion 455 couples with the suture tab assembly connection block 452 and with a force limiting connector 456. The force limiting connector 456 includes a latch 458 that is configured to reversibly engage with a notch 459. FIG. illustrates the case where the latch 458 is disengaged with the notch 459 as a result of the forces on the suture tube 451 increasing to the point that these forces overcome the engagement force of the latch 458 with the notch 459. Thus, in this embodiment the engagement force between the latch 458 and the notch 459 maintains the position of the suture tube 451 until the forces on the suture tube 451 have increased to the point that there is risk of damage to the suture and/or suture tube. After the latch 458 has become disengaged from the notch 459, the implant deployment device can be manually moved to a position in which the suture tab assembly 450 can be reset such that the latch 458 is reengaged with the notch 459. From this reset position, proper deployment of an implant can then be attempted.

In several of the embodiments disclosed herein, the handle and cartridge system is designed to function properly and deliver an implant when the needle travels a desired distance beyond the distal portion of the distal end of the cartridge elongate assembly. Similarly, the handle and cartridge system is designed to function properly and deliver an implant when the needle and implant maintain desired relative positions during a step in the implant process. The force limiting springs and force limiting connectors disclosed herein assist in preventing damage to elements within the cartridge and handle system when the system is not functioning in a way that it can successfully deliver an implant.

Figure 7:
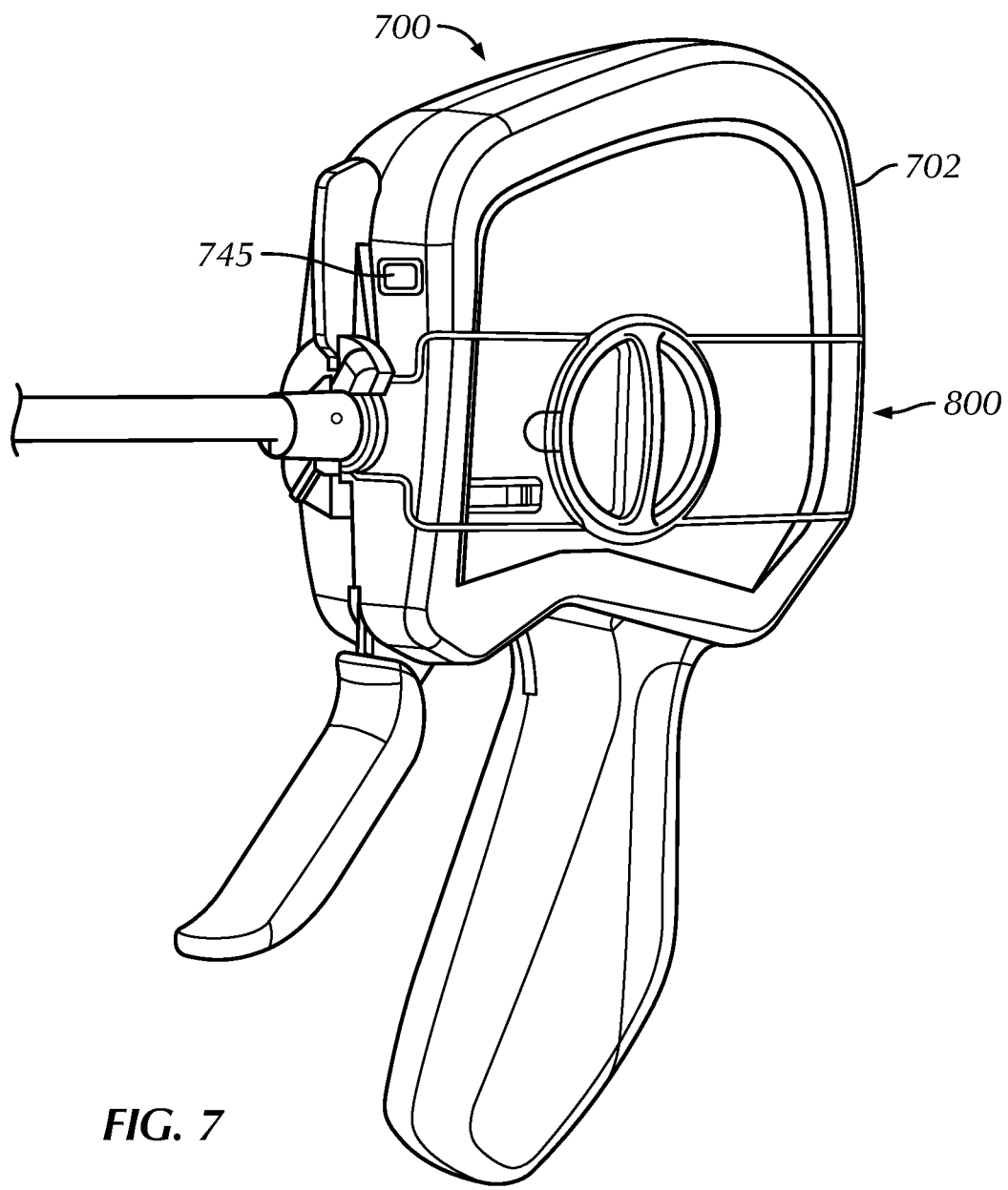
FIG. 7 is an isometric view of handle and cartridge system having a deployment indicator according to another embodiment of the invention.

According to certain aspects of embodiments disclosed herein, the handle and cartridge system include position indicators that alert a user to certain conditions in which the handle and cartridge system may be unable to successfully deliver an implant. FIG. 7 illustrates an isometric view of a handle and cartridge system similar to those illustrated in FIG. 1 and FIG. 2A. A cartridge 800 is shown as inserted and engaged with a handle 700. A left handle case 702 includes a front opening in which a needle sled button 745 travels. The needle sled button 745 is coupled to a needle sled within the handle 700 (such as the needle sled 140 illustrated in FIG. 1). The needle sled button 745 is configured such that when the needle sled 140 is in a proximal position and the needle of the cartridge is undeployed, a user can tactilely identify that there is a front opening in the left handle case 702. When the needle sled 140 moves fully forward and deploys the needle to its full extent of deployment out of the distal end portion of the cartridge elongate assembly, the needle sled button 745 moves forward within the front opening in the left handle case 702 such that the needle sled button 745 is flush with the front surface of the left handle case 702. In this configuration, a user can tactilely identify that the front opening in the left handle case 702 is completely filled by the needle sled button 745.

In a case where the needle does not completely deploy to its full extent of deployment out of the distal end portion of the cartridge elongate assembly, the needle sled button 745 will not completely fill the front opening in the left handle case 702. In this case, as user can tactilely identify that there has been incomplete deployment of the needle and the user can take steps to reset the device and attempt deployment again. Thus, the needle sled button 745 provides another mechanism to reduce or prevent damage to the needle, the implant, the suture, or to other mechanisms within the handle and cartridge system.

Figure 8:
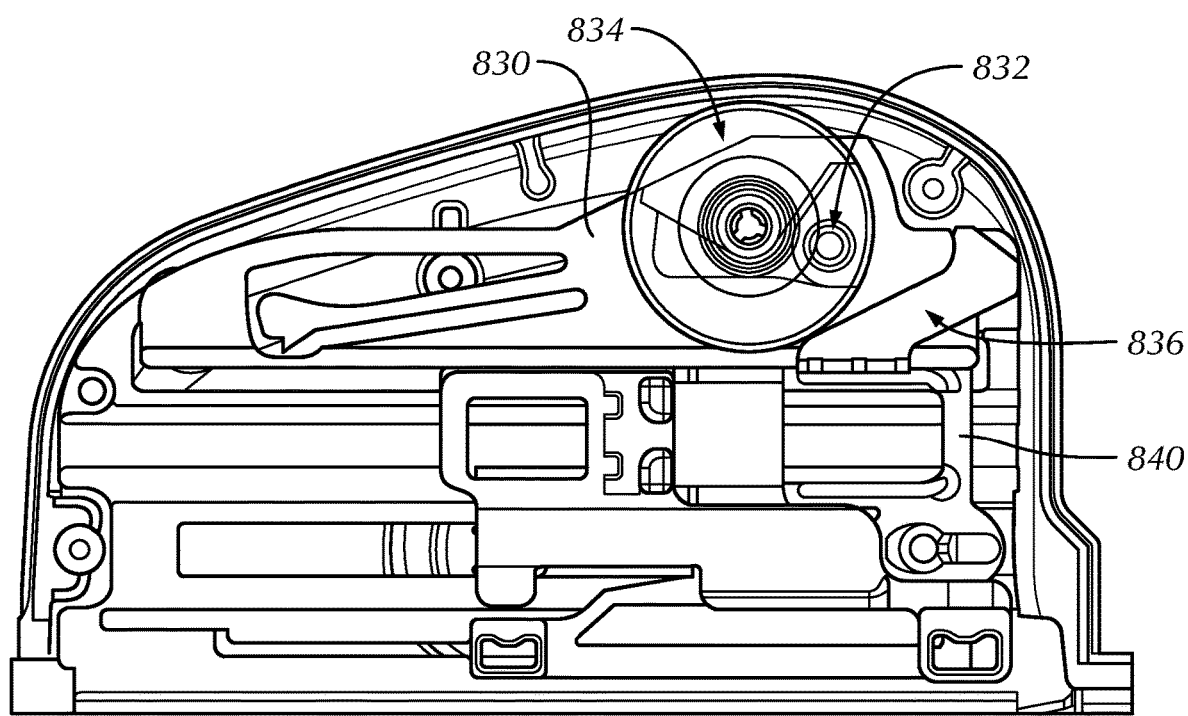
FIG. 8 is a side view of a section of a handle having a deployment indicator according to another embodiment of the invention.

In another embodiment, the needle sled includes a mechanism that visually or audibly alerts a user that the needle has not completely deployed or that the needle has completely deployed. For example, referring again to FIG. 8, the cover plate 830 (similar to the cover plate 130 of FIG. 1) is modified to include a mounting post for a semi-spherical bell 834. The cover plate 830 also includes a feature to mount a bell spring 832. The bell spring 832 sticks up into the interior of the bell 834 (this configuration saves space as compared to a bell striker mounted externally to the bell). The needle sled 840 is modified to include an alert arm 836 that contacts the bell spring 832 as the needle sled 840 moves distally during a needle deployment step as described elsewhere herein. The alert arm 836 causes the bell spring 832 to bend over as the alert arm passes underneath the bell 834. That is, the alert arm 836 folds the bell spring 832 over as the alert arm 836 moves distally. The alert arm 836 is configured such that is releases the bell spring 832 when the needle sled 840 has moved distally to a position that corresponds with complete deployment of the needle. The released bell spring 832 pops up and strikes the bell 834, indicating to the user that the needle is completely deployed. Thus, if the user does not hear the bell, the user can take steps to reset the system and redeploy the needle. To prevent the bell 834 from ringing again when the needle sled 840 is repositioned to the initial position and the end of a deployment sequence, the alert arm 836 includes a ramp feature that temporarily moves the bell spring 832 to the side instead of folding the bell spring 832. Moving the bell spring 832 to the side allows the bell spring 832 to return to its original position without ringing the bell 834. One advantage of this design is that it is not sensitive to the speed of the needle sled. Because the force used to strike the bell is that generated by the folded spring, a slow moving sled or a fast moving sled will generate the same amount of audible signal.

The embodiments disclosed herein contain aspects that indicate the complete deployment of a needle and/or the incomplete deployment of a needle. There are aspects of embodiments that prevent damage to a needle assembly or to a suture assembly and allow for a manual reset. There are aspects of embodiments that prevent damage to a needle assembly or to a suture assembly and assist in resetting the device. Each of these aspects may be used in combination with each other where their use is compatible. For example, there may be an embodiment that includes a deployment indicator and also includes a force limiting feature. That force limiting feature may allow for manual resetting, automatic resetting, or both. The separate description of embodiments is not intended to preclude their use in combination.

Other treatment devices may benefit from the use of the embodiments disclosed herein. Treatment devices equipped with various tools which manipulate, ablate, or otherwise alter tissue, where those tools are moved, deployed, or driven by mechanical energy, can benefit from the use of the force limiting springs and connectors disclosed herein, as well as the use of the deployment indicators disclosed herein. Such tools can include, but are not limited to, needles, cutting blades, vacuums, grasping arm assemblies, expandable cutting members, blunt dissectors, noose or ligature clips, articulating heads with an integral or retractable blade, helical blades, electrodes for delivery of radiofrequency energy, cutting wires or rings, electrocauterizing probes, or staple or suture delivery heads.

In some embodiments, a treatment device can include an introducer with a lumen carrying the tool, and a handle assembly coupled to the introducer. The treatment device includes a pusher, sled, or delivery mechanism that moves the tool forward thereby unsheathing the tool from the distal end of the introducer. This can be done by an actuator or trigger of the handle assembly.

In certain embodiments, a treatment device can be an apparatus that deploys one or more implants to retract, lift, compress, support, remodel, or reposition tissue within a patient's body. The treatment device can deliver a first or distal anchor component at a first location within a patient's body and a second or proximal anchor component at a second location within the patient's body. The treatment device can also impart tension to a connector that attaches the first and second anchors.

In some embodiments, the treatment device includes a cartridge carrying at least one implant and a handle configured to receive the cartridge. The handle includes an actuator and at least one spring mechanism loaded with mechanical energy. The handle also includes a member that mates with the cartridge to transfer mechanical energy from the spring mechanism to the cartridge for deploying the implant. The handle and cartridge system includes a first firing sled that has slots aligning with pusher tabs on a needle assembly. The slots of the first firing sled and the pusher tabs of the needle assembly are complementary mechanisms that allow for the transfer of energy from the spring mechanism via the first firing sled to fire a needle in the cartridge. The handle and cartridge system can also include a second firing sled with slots aligning with pusher tabs on a suture tube or connector tube. The slots of the second firing sled and the pusher tabs of the suture tube are complementary mechanisms that allow for the transfer of energy from the spring mechanism via the second firing sled to advance the suture tube simultaneously with the needle tube.

Other treatment devices may also use movable parts employing mechanical energy to introduce tools to an interventional site. If the tools strike bone, calcifications, or other solid or hard anatomical structures, it can cause damage to the tools and/or the movable parts within the treatment device. In some cases, although there may not be damage to the tool or the movable parts, the deployment of the tool will be unsuccessful if the tool strike such non-target tissue.

An apparatus for preventing, or at least reducing, deployment failure of a needle, penetrating member, or other tool due to bone strikes (or striking other non-target tissue) can include an adjustable, compressible, extendable, or resettable element coupled to the movable parts in a treatment device. In some embodiments, such as when a treatment device includes a connector or tensioning element, the apparatus can prevent, or at least reduce, buckling of the connector due to bone strikes.

While particular elements, embodiments and applications of the present invention have been shown and described, it will be understood that the invention is not limited thereto since modifications can be made by those skilled in the art without departing from the scope of the present disclosure, particularly in light of the foregoing teachings.

We claim:

1. An apparatus for manipulating tissue within a subject to treat a medical condition, the apparatus comprising:
   a first movable assembly coupled to a needle;
   a second movable assembly coupled to a suturing component, wherein the first movable assembly and the second movable assembly are configured to move relative to each other;
   a force limiting element coupled to the second movable assembly and a proximal portion of the suturing component, wherein the force limiting element is configured to maintain a position of the second movable assembly relative to the first movable assembly; and
   an implant configured for deployment within the tissue, the implant comprising one or more anchor members connected to a tensioning element.

2. The apparatus of claim 1, wherein the suturing component comprises an elongate tubular member defining an inner lumen configured to accommodate a suture.

3. The apparatus of claim 1, wherein the first movable assembly is configured to move proximally relative to the second movable assembly.

4. The apparatus of claim 1, wherein the force limiting element comprises a spring.

5. The apparatus of claim 4, wherein a portion of the suturing component is configured to extend through a lumen defined by coils of the spring.

6. The apparatus of claim 4, wherein the spring is a tension spring configured to extend in response to an increase in frictional force received at a distal end of the needle.

7. The apparatus of claim 1, wherein the force limiting element comprises a latch configured to reversibly couple with a complementary notch defined by the second movable assembly.

8. The apparatus of claim 7, wherein the latch is configured to disengage from the notch in response to an increase in frictional force received at a distal end of the needle.

9. The apparatus of claim 1, wherein manipulating comprises retracting, lifting, compressing, displacing, approximating, supporting, remodeling, repositioning, ablating, or altering at least a portion of the tissue.

10. The apparatus of claim 1, wherein the tissue comprises a prostate gland.

11. The apparatus of claim 1, wherein a portion of the suturing component extends through a passage defined by the second movable assembly.

12. The apparatus of claim 11, further comprising a friction element configured to conditionally prevent the suturing component from moving proximally through the passage.

13. The apparatus of claim 12, wherein a cross section of the suturing component is greatest at the friction element.

14. A cartridge for delivering an implant, comprising:
   a housing;
   a movable assembly positioned within the housing and coupled to a suturing component, the suturing component comprising a suture and an elongate tubular member defining an inner lumen configured to accommodate the suture, wherein the movable assembly is configured to move relative to the housing; and
   a force limiting element coupled to the movable assembly and a proximal portion of the suturing component, the force limiting element configured to absorb frictional forces received at a distal portion of the suturing component during delivery of the implant to a tissue.

15. The cartridge of claim 14, wherein the force limiting element comprises a latch configured to reversibly couple with a complementary notch defined by the movable assembly.

16. The cartridge of claim 14, wherein the force limiting element comprises a spring.

17. The cartridge of claim 14, further comprising a needle and an elongate assembly, wherein the needle is configured to slide longitudinally through the elongate assembly during delivery of the implant.

18. An apparatus for manipulating tissue within a subject to treat a medical condition, the apparatus comprising:
   a first movable assembly coupled to a needle;
   a second movable assembly coupled to a suturing component, wherein the first movable assembly and the second movable assembly are configured to move relative to each other;
   a force limiting element coupled to the second movable assembly and a proximal portion of the suturing component, wherein the force limiting element is configured to maintain a position of the second movable assembly relative to the first movable assembly, wherein the force limiting element comprises a spring, and a portion of the suturing component is configured to extend through a lumen defined by coils of the spring.

* * * * *